United States Patent [19]

Donald et al.

[11] Patent Number: 4,501,896

[45] Date of Patent: Feb. 26, 1985

[54] PHENYLMERCAPTOTETRAZOLO- AND NITROINDAZOLO MASKED DEVELOPMENT/IMAGE MODIFIERS

[75] Inventors: Dennis S. Donald, Mendenhall, Pa.; Ross A. Lee, Webster, N.Y.

[73] Assignee: E. I. du Pont de Nemours and Company, Wilmington, Del.

[21] Appl. No.: 290,497

[22] Filed: Aug. 6, 1981

Related U.S. Application Data

[62] Division of Ser. No. 172,999, Jul. 25, 1980, Pat. No. 4,343,893.

[51] Int. Cl.$^3$ ................... C07D 257/02; C07D 231/54
[52] U.S. Cl. ...................................... 548/251; 548/371
[58] Field of Search ................................ 548/251, 371

[56] References Cited

U.S. PATENT DOCUMENTS

3,993,661  11/1976  Grashoff .............................. 548/251
4,187,110  2/1980  Yagihara et al. ..................... 430/544

*Primary Examiner*—Glennon H. Hollrah
*Assistant Examiner*—D. B. Springer

[57] ABSTRACT

Novel nitrobenzyl compounds are incorporated into a photographic emulsion or developer for controlled release of development/image modifier compounds. This occurs imagewise only after developer oxidation products have been formed in the course of the development process. For example, nitrobenzyl-masked phenylmercaptotetrazole (PMT), incorporated into a silver halide emulsion, reacts with developer oxidation products via an electron transfer mechanism to release the potent development restrainer PMT.

17 Claims, No Drawings

PHENYLMERCAPTOTETRAZOLO- AND NITROINDAZOLO MASKED DEVELOPMENT/IMAGE MODIFIERS

This is a division of application Ser. No. 172,999, filed July 25, 1980 now U.S. Pat. No. 4,343,893.

FIELD OF THE INVENTION

The present invention deals with photographic silver halide elements which upon exposure will react with photographic developers to product silver images, and particularly with the release of masked development-/image modifier compounds during the development process.

BACKGROUND OF THE INVENTION

In the class of photographic arts which employs as the photographic element a support carrying a light-sensitive silver halide emulsion layer, it is known to incorporate into the emulsion a protected antifoggant, e.g., certain derivatives of 1-phenyl-5-mercaptotetrazole (PMT). The object is to release PMT when the exposed emulsion is processed in an alkaline developer solution. When thus released, PMT restrains fog. Having a potent compound safely stored within an emulsion by being chemically bound up as a derivative until it is chemically released has many potential benefits. But one disadvantage is that such release occurs throughout the emulsion layer, without regard for imaged or non-imaged areas, and the active compound becomes immediately functional when the requisite degree of alkalinity is achieved. The same result would follow if one were to incorporate the protected antifoggant directly into the alkaline developer formulation. Another disadvantage is that the early release of the antifoggant in the development process retards development, adversely affects sensitometry, and does nothing to improve covering power and silver utilization generally.

The present invention makes it possible to retain the advantages of a protected antifoggant while at the same time obtaining more efficient utilization of silver, improved image quality, and better development latitude.

SUMMARY OF THE INVENTION

This invention is directed to a new class of compounds which is useful in the light-sensitive photographic art as masked development/image modifier compounds; and to photographic films, photographic developer solutions, and photographic development processes which employ such compounds. A typical example of such development/image modifying compounds is a masked antifoggant. Using this as an illustration, the term "masked" means that the antifoggant is employed in the form of a derivative which keeps the antifoggant moiety inactive until image formation in the photographic developer has commenced, whereupon cleavage or unmasking occurs in those areas of the emulsion where chemical development takes place to form a silver image. The term "masked antifoggant" is distinguished from the prior art term "protected antifoggant" in that an increase in pH is necessary in order to release the protected antifoggant of the prior art, whereas electron transfer releases the masked antifoggant of this invention.

Compounds which are effective for use in the present invention have the structural formula:

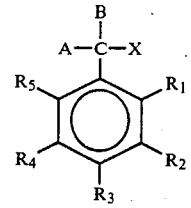

wherein
A = alkyl, alkylcarboxyalkyl, or hydrogen;
B = alkyl, hydrogen, or carboxyalkyl;
$R_1$ to $R_5$ = hydrogen, halogen, —$CF_3$, cyano, or nitro; and
X is a radical which, after release, forms a member of the photographically active group consisting of antifoggants, toners, spectral sensitizers, dyes, color couplers, silver halide solvents, stabilizers, hardeners and accelerators.

In the case of a masked antifoggant X is a radical which, after release, forms either 1-phenyl-5-mercaptotetrazole, 5 nitroindazole, phenidone, or 3,4,5, 6-tetrahydro-2-pyrimidinethiol.

DETAILED DISCLOSURE OF THE INVENTION

The electron transfer mechanism is believed to be in accordance with the literature disclosure of Nathan Kornblum, Angew. Chem. Internat. Edit., p. 734, V. 14, No. 11 (1978). Within the concept of the present invention a compound is provided having an organic ring structure with substituents such that a net electron withdrawing effect exists at the benzyl position. During development of such an emulsion an electron is transferred to the compound by reaction with oxidized developing agent. Within the terminology of the organic chemist the electron withdrawing effect is achieved by choosing substituents whose Hammett sigma functions sum to a value of $\sigma = 0.50$ to 1.00, with the preferable range being $\sigma = 0.60$ to 0.80. This can be illustrated by the selection of R groups on the organic ring structure.

Among the R groups which may be attached to the ring, the nitro, halogen, —$CF_3$, and cyano groups are particularly effective as electron-withdrawing substituents. Because of the recognized distinction between meta- and ortho- or para-ring substitution, the Hammett sigma functions become useful in choosing R groups. By reference to tables such as Table 5 at p. 241 of Advanced Organic Chemistry: Reactions, Mechanisms, and Structures; Jerry March, McGraw Hill, one selects R substituents whose Hammet sigma functions add up to a value: $\sigma = 0.50-1.00$. This method is preferable to the empirical approach of synthesizing the compounds and testing to determine if they will react with developer oxidation products to accept an electron.

For a compound to be useful within the concept of the present invention it must (1) be compatible with the system, i.e., with the photographic elements or solutions, with which it is to be used, and (2) be stable within the system prior to time of use. It is important that the electron-withdrawing functionality of the ring not be either too much or too little to allow the compound to remain inactive within the photographic system prior to the triggered release by electron transfer. If the electron-withdrawing functionality is too much, the molecule is unstable and can be released prematurely. If too little, the compound cannot be released in the development process. A photographic film constitutes an extremely sensitive photochemical environment, and to be useful therein the compound must not adversely affect that environment.

It is not intended to limit the present invention to any particular silver imaging system. As long as the imaging process includes a development or reduction step in order to convert silver compound or complex to metallic silver, that step will provide the electron transfer which is necessary to unmask the compounds of the present invention in the areas of the emulsion which are developing. The present invention is operative with conventional developing agents such as described in chapter 11 of the Fourth Edition of The Theory of The Photographic Process, e.g., hydroquinone, catechol, aminophenol, pyrogallol, pyrazolidone, phenylenediamine, etc.

It is envisioned that the present invention can be applied to all silver imaging systems, and even to other systems which involve a similar chemical development step, i.e. one whereby a product of the developing reaction provides the means for electron transfer to compounds of this invention by reason of their electron-withdrawal capability. Within the scope of silver image formation, semiquinone is formed and is a particularly active species for electron transfer. Systems which produce a nonsilver dye image, such as color development, contain analogous active species such as quinonediimine. Since the present invention does not rely on an increase in pH for activation, the electron transfer could be initiated in a thermographic or photopolymerization process.

It is a particularly useful feature of the present invention that the masked derivatives can be simply added to a photographic emulsion without the necessity of rebalancing the formulation, as is often the case in the art. This represents an extremely valuable feature.

A number of illustrative masked development/image modifying compounds of the present invention are set forth below by means of a listing of substituents to the general formula:

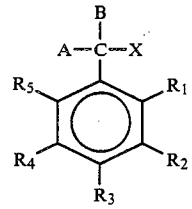

| Masked Compound | A | B | $R_1$ | $R_2$ | $R_3$ | $R_4$ | $R_5$ |
|---|---|---|---|---|---|---|---|
| 1 PMT | H | H | H | H | $-NO_2$ | H | H |
| 2 PMT | H | H | $-NO_2$ | H | H | H | H |
| 3 PMT | H | H | $-NO_2$ | H | $-NO_2$ | H | H |
| 4 PMT | H | H | Cl | H | $-NO_2$ | H | H |
| 5 PMT | H | H | H | $-NO_2$ | H | $-NO_2$ | H |
| 6 PMT | $-CH_3$ | $-CH_3$ | H | H | $-NO_2$ | H | H |
| 7 PMT | H | $-CH_2CO_2H$ | H | H | $-NO_2$ | H | H |
| 8 PMT | H | $-CH_2CO_2H$ | $-NO_2$ | H | $-NO_2$ | H | H |
| 9 PMT | H | $-CH(CH_3)CO_2H$ | H | H | $-NO_2$ | H | H |
| 10 PMT | H | $-C(CO_2C_2H_5)_2CH_3$ | H | H | $-NO_2$ | H | H |
| 11 PMT | H | $-C(CO_2C_2H_5)(CO_2H)CH_3$ | H | H | $-NO_2$ | H | H |
| 12 5-NI | H | H | H | H | $-NO_2$ | H | H |
| 13 5-NI | H | H | $-NO_2$ | H | H | H | H |
| 14 Phenidone | $-CH_3$ | $-CH_3$ | H | H | $-NO_2$ | H | H |
| 15 THPT.HCl | H | H | H | H | $-NO_2$ | H | H |
| 16 THPT.HCl | H | H | H | $-NO_2$ | H | $-NO_2$ | H |

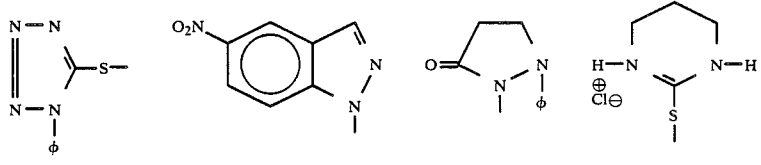

PMT     5-NI     Phenidone     THPT—HCl

The invention is illustrated by the following examples.

EXAMPLE 1

Compound 1: 1-phenyl-5-(p-nitrobenzylthio)tetrazole

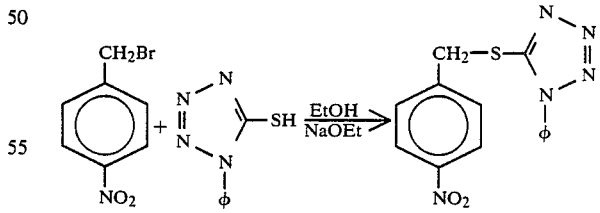

To a flame-dried, 2-liter, 3-necked, round bottomed flask equipped with mechanical stirrer, thermometer and nitrogen inlet was added 500 ml of absolute ethanol followed by 5 g (0.217 mol) of sodium metal; the mixture was stirred at ambient temperature under nitrogen. After all of the sodium had reacted, the homogeneous solution was cooled to 10° C. in an ice bath and 35.6 g (0.200 mol) of 1-phenyl-5-mercaptotetrazole (PMT) was added all at once. A homogeneous solution was obtained within ten minutes whereupon 43 g (0.200 mol) of p-nitrobenzylbromide was added all at once. The ice bath was allowed to melt and the reaction mixture was stirred under nitrogen at room temperature for two days. After cooling to 0° C. the slurry was filtered and the solid was washed twice with 500 ml portions of cold ethanol, twice with 100 ml portions of water, and air dried, yielding 59 g (94%) of crude product which was virtually pure by NMR. Recrystallization from dimethyl formamide gave 28.8 g of white needles, mp. 154°–156° C.

Compound 2: 1-phenyl-5-(o-nitrobenzylthio) tetrazole

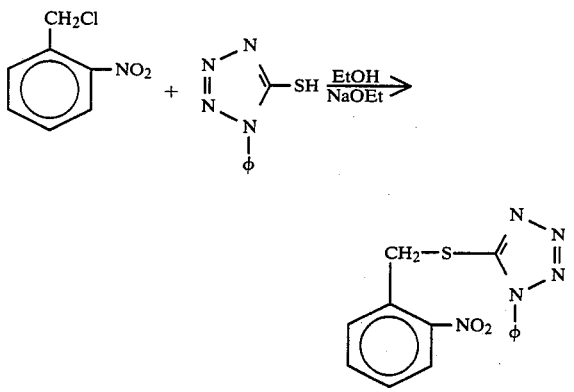

This compound was prepared according to the method of Compound 1, on a 0.10 mol scale and 20 hr reaction time; crude yield=95%. Recrystallized from dimethyl formamide, it formed lustrous plates, mp 158°–161°.

Compound 3: S(2,4-dinitrobenzyl)-phenylmercaptotetrazole

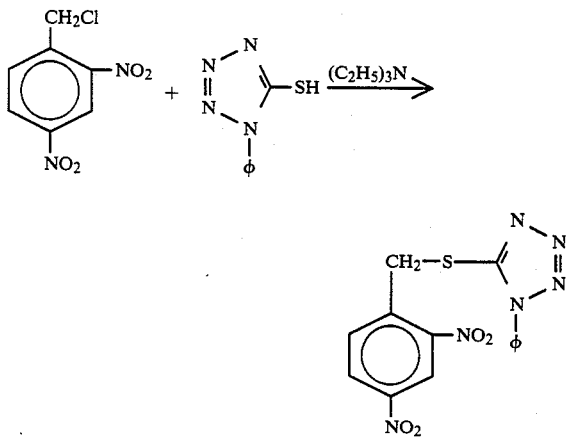

In a 100 ml, round-bottomed, 3-necked flask equipped with magnetic stirrer, thermometer and nitrogen cap was placed 4.35 g (0.020 mol) of 2,4-dinitrobenzylchloride, 50 ml tetrahydrofuran, and 3.56 g (0.02 mol) phenylmercaptotetrazole. To the resulting homogeneous solution at room temperature was added all at once 21 g (0.023 mol) of triethylamine. The temperature rose quickly to 30° then returned slowly to ambient. After stirring overnight the reaction mixture was poured, with good stirring, into 200 ml of 2N HCl and the precipitate was collected by filtration, washed with water and air dried to 7.15 g. Recrystallization from ethanol gave 4.80 g (67%) of compound 3 as lustrous, off-white plates, mp. 113.0°–114.0° C.

Compound 4: (o-chloro-p-nitrobenzyl)-phenylmercaptotetrazole

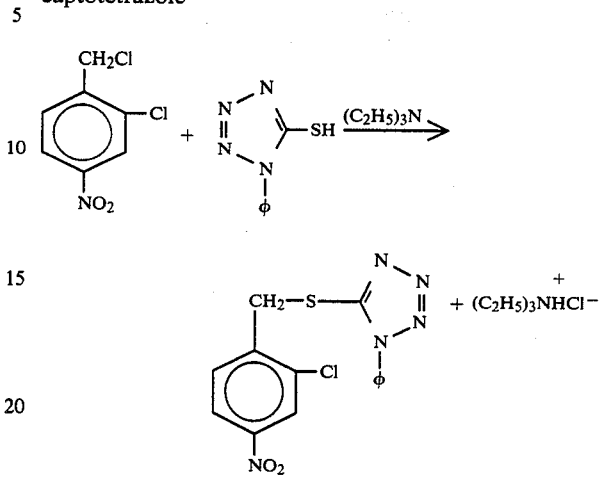

To a solution of 10.3 g (0.05 mol) of o-chloro-p-nitrobenzyl chloride and 8.90 g (0.05 mol) phenylmercaptotetrazole in 100 ml dry THF under nitrogen was added at once 5.1 g (0.05 mol) of triethylamine. The temperature rose slowly to 30° C. and solid began to precipitate. After stirring overnight 5.94 g of white triethylamine hydrochloride was filtered off (theory 6.88 g) and the filtrate was taken to dryness. The solid residue was recrystallized from methanol, giving compound 4 as off-white crystals that melted with decomposition at 94° C.

Compound 5: (3,5-dinitrobenzyl)phenylmercaptotetrazole

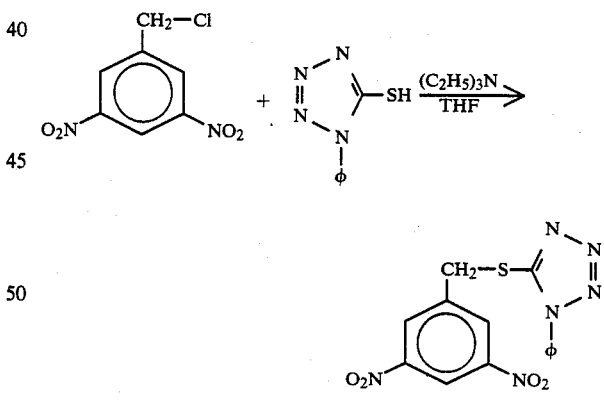

To a solution of 50 g (0.231 mol) of 3,5-dinitrobenzylchloride and 41 g (0.231 mol) of phenylmercaptotetrazole in one liter of dry tetrahydrofuran under nitrogen was added all at once with stirring 23.4 g (0.231 mol) of triethylamine. The temperature rose slowly from 23° to 29°. After stirring overnight the reaction mixture was diluted with one liter of water, cooled to 10° C., filtered and the filter cake was washed well with water. Oven drying at 110° C. for 24 hours gave 78 g (83%) of product mp. 156°–158° C. Recrystallization from tetrahydrofuran gives analytically pure 5, mp. 161.5°–162.5° C.

Compound 6: 1-phenyl-5-(p-nitrocumylthio)tetrazole

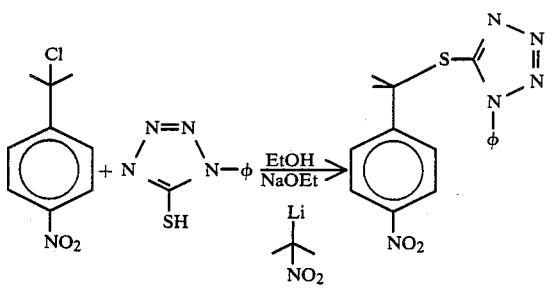

Prepared according to the method of Compound 1 on a 0.025 mol scale with the following modification: after 20 hr very little, if any reaction had occurred as indicated by an insignificant amount of sodium chloride precipitate. The lithium salt of 2-nitropropane was added as an "entrainment catalyst". Within 15 minutes there was a significant amount of precipitate and after stirring overnight the reaction mixture was nearly solid with precipitate. The usual work-up gave a 53% crude yield of material which was recrystallized from ethanol, mp. 122.0°–122.5° C.

Compound 7: β-phenylmercaptotetrazolo-β-p-(nitrophenyl) propanoic acid

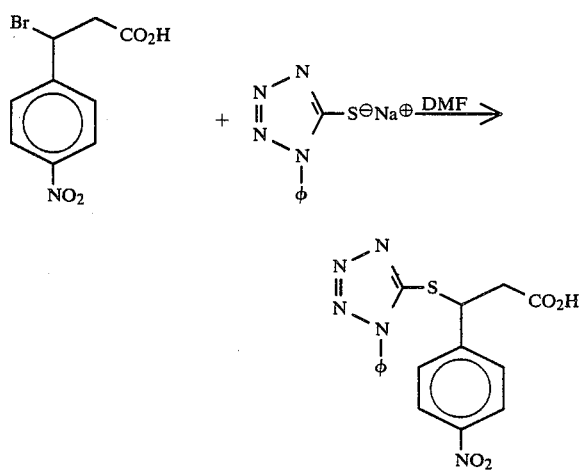

In a flame dried, 200 ml, 2-necked, round-bottomed flask equipped with magnetic stirring, nitrogen inlet tube and nitrogen outlet cap connected to a mineral oil bubbler, was placed 13.7 g (0.05 mol) of the benzyl bromide, 100 ml of dry dimethylformamide, 10 g (0.05 mol) of the sodium salt of phenylmercaptotetrazole and 400 mg (4 mmol) of the lithium salt of 2-nitropropane. The homogeneous reaction mixture was stirred at room temperature for 70 hours as a very slow stream of dry nitrogen was passed through to remove inhibiting oxygen. It was then poured slowly into 500 ml of water whereupon an oil formed which solidified upon stirring for 2 hours. Filtration, washing with three 25 ml portions of water, and air drying gave 16 g (87%) of cream-colored solid melting at 164.5° C. with decomposition. Recrystallization from methanol gave compound 7 as pale yellow needles, mp. 167° C. with decomposition.

Compound 7 was placed in an aqueous solution at a pH of 10.2 for a period of 24 hours. It was determined that the compound did not undergo reaction or cleavage. This illustrates the hydrolytic stability of the compounds of the present invention and distinguishes them from the prior art compounds which release the active species in alkaline solution.

Compound 8: 3-(2,4-dinitrophenyl)-3-S(2-phenyl-1-mercaptotetrazole) propanoic acid

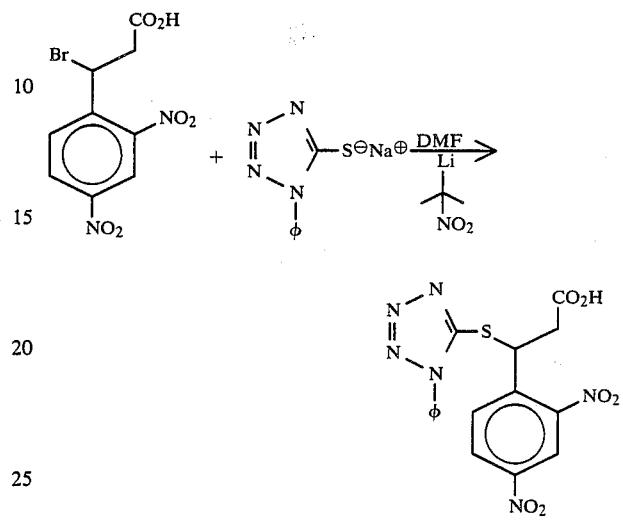

A 100 ml, 2-necked, round-bottomed flask equipped with a gas inlet tube, nitrogen cap and magnetic stirrer was dried with a heatgun under nitrogen. After cooling, 40 ml of dry DMF, 6.38 (0.02 mol) of benzylbromide, 8 g (0.04 mole) of the sodium salt of phenylmercaptotetrazole and finally 160 mg of the lithium salt of 2-nitropropane were added. A very slow stream of nitrogen was bubbled through the homogeneous reaction mixture to remove inhibiting oxygen. The reaction mixture slowly turned red-orange over the next three hours. After stirring overnight the reaction mixture was poured into 200 ml of water and the mixture extracted well with methylene chloride. Back extraction of the combined methylene chloride solution with three 100 ml portions of water was followed by drying (MgSO4) and stripping on a rotatory evaporator. The residue appeared to be ca. 80% desired product by NMR. An oily by-product appeared to be the olefin formally derived by elimination of HBr. The crude product was dissolved in hot isopropanol and filtered. After standing two days at 5° C. there was deposited 2 g of pale yellow crystals, mp. 150°–155° C. with decomposition and gas evolution.

Compound 9: β-(phenyl mercaptotetrazolo-β-(p-nitrophenyl)-α-methyl propanoic acid

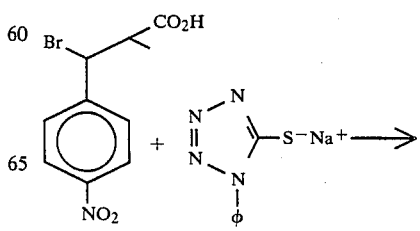

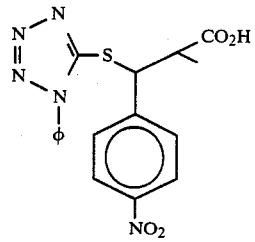

A solution of 4.32 g (0.015 mol) of the acid, 3 g of the sodium salt of phenylmercaptotetrazole and 120 mg of the lithium salt of 2-nitropropane in 10 ml of dry dimethyl formamide was stirred at room temperature for 40 hours with a very slow stream dry nitrogen passing through. The reaction mixture was poured into 150 ml of water and the whole was extracted well with diethyl ether. The ether solution was back-washed with water and brine and dried over anhydrous magnesium sulfate. Removal of the solvent gave a semisolid which was triturated with methylene chloride giving 0.3 g of an insoluble by-product upon filtration. Removal of the methylene chloride from the filtrate gave 3.5 g of an orange oil whose NMR spectrum indicates that it is a one-to-one mixture of the two diastereomeric pairs expected. Trituration with carbon tetrachloride gives 2.5 g of solid which has been enriched to 72% of one diastereomer of compound 9. The material was used in this form.

Compound 10: 2,2-dicarboethoxy-3-(phenylmercaptotetrazolo)-3-(p-nitrophenyl)propane

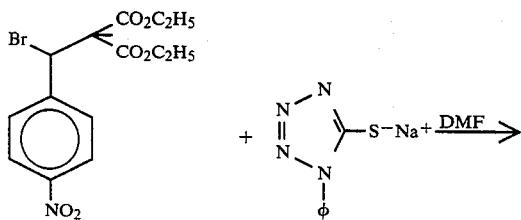

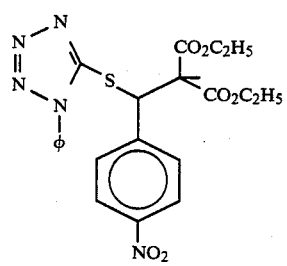

A solution of 20 g (0.0515 mol) of the benzylbromide, 12 g (0.060 mol) of the sodium salt of phenylmercaptotetrazole, and 0.50 g (5.2 mol) of the lithium salt of 2-nitropropane in 100 ml of dry dimethylformamide was stirred with a slow stream of nitrogen passing through and a sun lamp at about six inches shining on it. A sample analyzed by NMR after 24 hr indicates a 60% conversion. After 48 hr the conversion was at least 80%, and at least 95% at 65 hr. After 70 hours the entire reaction mixture was poured into 500 ml of brine and the resulting mixture was extracted three times with 200 ml portions of chloroform and the combined extracts were back-extracted with two 100 ml portions of water. After drying (MgSO$_4$), filtering, and stripping on a rotatory evaporator, the residue was subjected to high vacuum and mild heat to remove the last traces of dimethylformamide. The NMR spectrum indicates complete conversion.

Compound 11: 2-carboethoxy-2-methyl-3-(phenylmercaptotetrazolo)-3-(p-nitrophenyl)propanoic acid

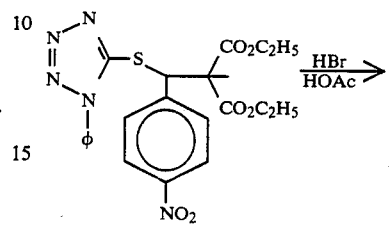

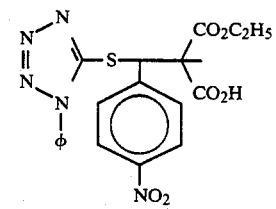

A mixture of 9 g (0.0185 mol) of the diester, 100 ml of acetic acid, and 40 ml of 48% hydrobromic acid was heated at 70° for 66 hr and then was taken to an amber oil on a rotatory evaporator. This oil was then taken up in ca. 250 ml of diethylether and the resulting solution was extracted well with 10% sodium bicarbonate. The combined sodium bicarbonate extracts were acidified with 10% hydrochloric acid and the acidified solution was extracted well with diethyl ether. After drying (Na$_2$SO$_4$), filtering and evaporation on a rotatory evaporator, there remained 3.50 g of a mixture consisting of 68% of compound 11 and 32% of the acid shown below:

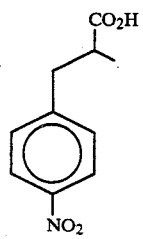

This mixture was used in Ex. 2 since the above acid would have no effect on photographic sensitivity or development in the procedure of Ex. 2.

Compound 12: 1-(p-nitrobenzyl)-5-nitroindazole

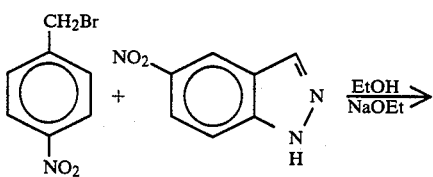

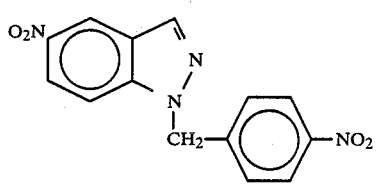

Prepared according to method of Example 1 on a 0.10 mole scale. Reaction time was only 4 hr but 29% of starting 5-nitroindazole was recovered. Crude yield 71%, recrystallized from ethanol, mp. 141°–142.5° C.

Compound 13: 1-(o-nitrobenzyl)-5-nitroindazole

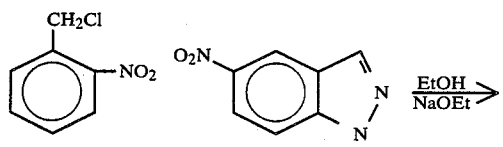

Prepared according to method of Compound 1 on a 0.05 mole scale and 17 hr reaction time, crude yield 67%. Recrystallized from methanol giving pale yellow needles, mp. 102°–103°.

Compound 14: N-(p-nitrocumyl)phenidone

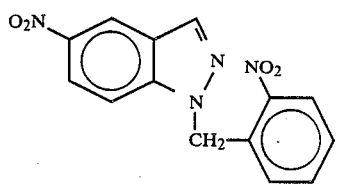

Prepared on a 0.01 mole scale by procedure of Compound 1 using 20 hr reaction time. A dark red, ethanol soluble by-product is formed in this reaction but is easily separated from the product simply by washing on the funnel. A 49% crude yield was obtained. Low temperature (−78° C.) recrystallization from methylene chloride gave a first crop (660 mg) of pure material, mp. 145.5–148.5. A second crop (600 mg) of slightly less pure material, mp. 144°–149.0° C., was obtained.

Compound 15: S-(o-chloro-p-nitrobenzyl)-3,4,5,6-tetrahydro-2-pyrimidinethiol hydrochloride

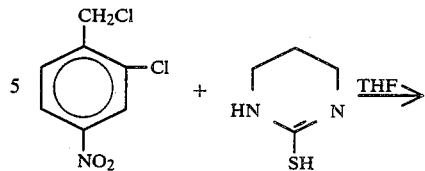

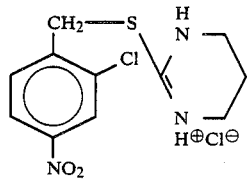

To 50 ml of dry tetrahydrofuran at room temperature under nitrogen was added all at once with stirring 5.1 g (25 mmol) of 2-chloro-4-nitrobenzyl chloride and 2.91 g (25 mmol) of 3,4,5,6-tetrahydro-2-pyrimidinethiol. The slurry warmed slightly and the consistency of the precipitate changed from granular to smooth. After stirring for 40 hours the precipitate was collected, rinsed with fresh tetrahydrofuran and recrystallized from i-propanol, giving 4.70 g of compound 15 as white crystals, mp. 220°–226° C. decomp.

Compound 16: S-(3,5-dinitrobenzyl)-3,4,5,6-tetrahydro-2-pyrimidinethiol hydrochloride

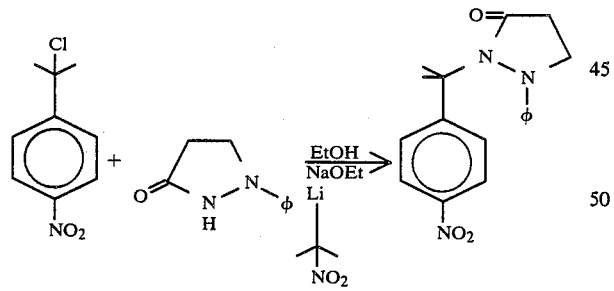

This compound was prepared by the method of Compound 15, mp. 240°–260° C. (ethanol).

Compound 17: p-nitrohydrocinnamic acid

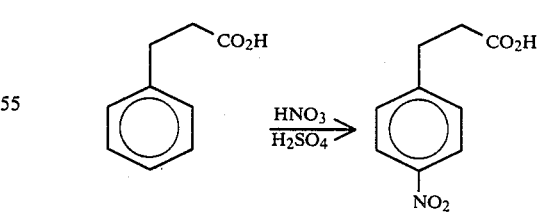

In a 2-liter, 3-necked, round-bottomed flask equipped with mechanical stirrer, thermometer, and additional funnel was placed 361 g (2.41 mol) of hydrocinnamic acid which was warmed to 50° to maintain it in a liquid state. To the warm liquid was added slowly dropwise over a 4 hour period with good stirring a mixture of 241 g of nitric acid and 546 g of sulfuric acid. The reaction is very exothermic so that a water cooling bath was required to which ice was added occasionally to keep the temperature at 50° C. The very thick reaction mixture was stirred for an additional 2 hours and poured onto 3 liters of ice. The solid was collected by filtration and washed repeatedly with a total of 6 liters of water. After air drying, the entire sample was recrystallized from 800 ml of acetone, giving a first crop of 150.4 g mp. 162°–164° C.

Compound 18: β-bromo-p-nitrohydrocinnamic acid

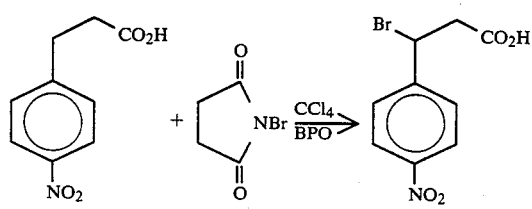

In a 1-liter, 1-necked, round-bottomed flask equipped with magnetic stirrer, condenser and nitrogen cap was placed 65 g (0.334 mol) of the acid, 65 g (0.368 mol) of N-bromosuccinimide, 1 g of benzoyl peroxide and 500 ml of carbon tetrachloride. The reaction mixture was heated at reflux overnight whereupon a copious precipitate had formed. This was removed by filtration at room temperature and the succinimide was removed by washing the solid well with warm water. The undissolved solid was oven dried at 60° to 77.5 g. Recrystallization from acetone gave material, mp. 166.0°–167.0° C.

Compound 19: 3-bromo-3-(2,4-dinitrophenyl)-propionic acid

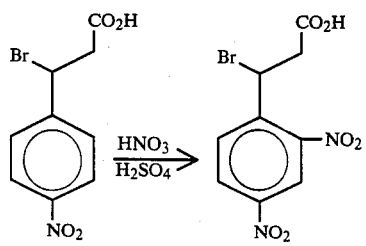

In a 1-liter, 3-necked, round-bottomed flask equipped with mechanical stirrer, thermometer, and 250 ml addition funnel was placed 200 ml of 90% fuming nitric acid followed by the portionwise addition of 54 g (0.20 mol) of 3-bromo-3-(4-nitrophenyl) propionic acid at 5°–10° C. To the resulting homogeneous solution was added dropwise over 45 min., 100 ml of concentrated sulfuric acid, keeping the temperature at 15°–20° C. with ice bath cooling. When the addition was complete the ice bath was removed and the reaction mixture was allowed to warm to room temperature. After an additional hour at room temperature the amber solution was poured onto 1 liter of ice. The gummy solid which formed was separated by decantation and stirred overnight in a liter of water giving a cream-colored solid which was collected by filtration and washed well with distilled water. After air drying, 40 g of crude product was recrystallized from nitromethane, giving 27 g of compound 19, mp. 157°–160° (decomp.) which gives a satisfactory NMR spectrum.

Compound 20: 3-bromo-3-phenylpropionic acid

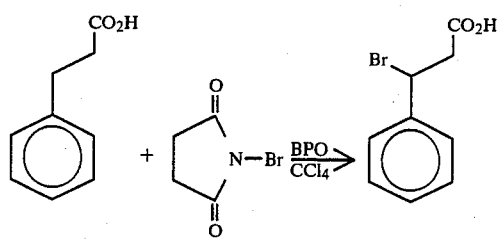

A mixture of 100 g (0.667 mol) of hydrocinnamic acid, 120 g (0.674 mol) of N-bromosuccinimide, and 1.8 g of benzoyl peroxide (BPO) in 900 ml of CCl₄ was heated at reflux for 20 hr under nitrogen. After cooling to room temperature the reaction mixture was filtered. The filtrate when stripped to dryness yielded only a small amount of additional material which was combined with the original solid and the whole was slurried for 2 hr with warm water to dissolve the succinimide. The slurry was filtered and rinsed with water again and oven dried at 50° C. overnight to 120.8 g (79%) of material which is pure enough for the next step. Material recrystallized from toluene melts 138.5°–140.0° C.

Compound 21: 2,2-dicarboethoxy-3-(p-nitrophenyl) propane

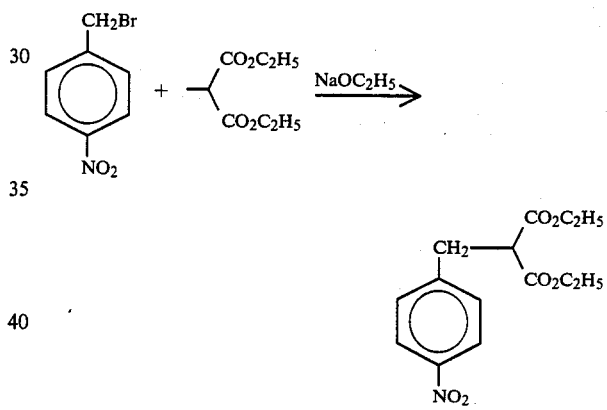

To a flame-dried 3-liter, 3-necked, round-bottomed flask equipped with mechanical stirrer, condenser, and addition funnel was added 750 ml of absolute ethanol followed by the portionwise addition of 26 g (1.15 mol) of sodium metal. After all the sodium had reacted and the reaction mixture had cooled to room temperature, the dropwise addition of 200 g (1.15 mol) of diethylmethyl malonate was made over a period of 1 hour. When the addition was complete the reaction mixture was heated at reflux for 15 minutes, cooled to room temperature, and the addition funnel was replaced with a gooch tubing connection through which 248 g (1.15 mol) of solid p-nitrobenzyl bromide was added slowly (exothermic) over 2 hours, keeping the temperature below 50° C. The homogeneous solution was heated at reflux for 2 hours and upon cooling to room temperature a copious precipitate formed. Filtration, water washing and air drying gave 187.1 g of white crystals. The ethanolic filtrate was taken to near dryness on a rotatory evaporator and the residue was taken up in water, filtered, water washed and air dried to 100 g. The infrared spectra of the two fractions were identical so they were combined and recrystallized from aqueous ethanol (1:3) giving, after drying in a desiccator over $P_2O_5$, 226.5 g (75%) of white granular compound 21. mp. 59°–61° C.

Compound 22: 2,2-dicarboxy-3-(p-nitrophenyl)propane

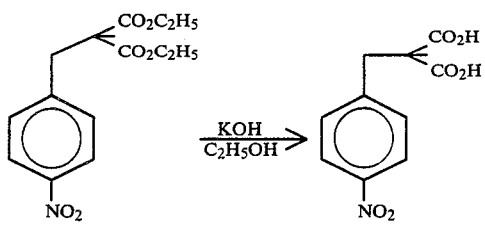

To a solution of 44 g (1.06 mol) of 85% potassium hydroxide in 350 ml of 95% ethanol was added 60 g (0.194 mol) of the diester and the whole was heated at reflux under nitrogen for 3 hours. The reflux condenser was replaced with a short distillation head and after 150 ml of distillate had been collected 300 ml of water was added and another 150 ml of distillate was removed. After cooling, the reaction mixture was extracted with diethyl ether to remove a small amount (<5 g) of unwanted material before acidifying with 6N hydrochloric acid. The solid which formed was extracted into diethyl ether (tends to emulsify), dried over anhydrous magnesium sulfate, filtered and evaporated on a rotatory evaporator to an orange oil which solidified upon standing. The entire sample was recrystallized from 100 ml of water giving 30.9 g (63%) of compound 22 in two crops; mp. 163° C. decomp.

Compound 23: β-(p-nitrophenyl)-α-methyl propanoic acid

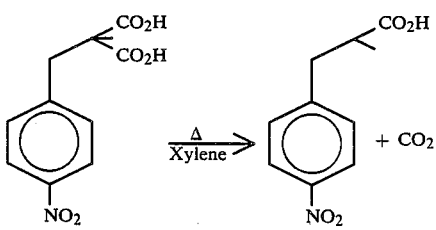

A slurry of 18 g (0.0727 mol) of the diacid in 100 ml of mixed xylenes was heated at reflux for 5 hours whereupon a nearly homogeneous, slightly dark solution was obtained. Decolorizing charcoal was added while the reaction mixture was still hot and filtration gave a pale yellow solution which, upon standing overnight at room temperature, deposited 11.5 g (76%) of compound 23 as light yellow crystals, mp. 117°–121° C.

Compound 24: β-bromo-β-(p-nitrophenyl-α-methyl propanoic acid

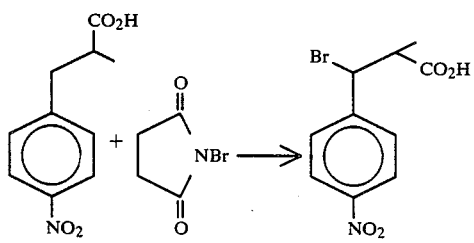

A mixture of 4.18 g (0.02 mol) of the acid, 3.92 g (0.022 mol) of N-bromosuccinimide, 50 mg of dibenzoylperoxide, and 25 ml of $CCl_4$ was heated at reflux for 2.5 hours. The cooled reaction mixture was filtered and the solid was washed with fresh $CCl_4$. NMR examination shows that the $CCl_4$ soluble material in the filtrate is mainly one of the desired diastereomeric pairs plus small amounts of the other pair and succinimide. The $CCl_4$-insoluble portion on the filter is a mixture of succinimide and the other diastereomeric pair. The solid on the filter was washed well with warm water to remove the succinimide, leaving after drying, 2.37 g of one pure diastereomeric pair as a cream-colored powder. This was used for further reactions.

Compound 25: 3-bromo-2,2-dicarboethoxy-3-(p-nitrophenyl) propane

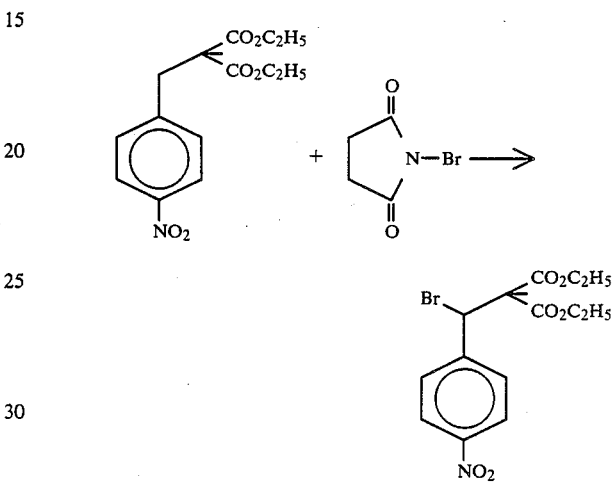

A mixture of 62 g (0.20 mol) of the diester, 39 g (0.22 mol) N-bromosuccinimide (NBS), 0.5 g of dibenzoylperoxide (BPO) and 500 ml of $CCl_4$ was heated at reflux. After 4.5 hours a sample examined by NMR indicated only 15% conversion. An additional 78 g more NBS and 1 g BPO was added and reflux continued for 20 hours. Sampling showed 52% conversion. Addition of another 78 g NBS, 1 g BPO and 20 hr reflux gave at least 86% conversion. Finally another 39 g NBS, 0.5 g BPO and 20 hr reflux gave complete conversion. The cold reaction mixture was filtered and washed well with carbon tetrachloride. The filtrate was washed well with water, dried over anhydrous sodium sulfate, filtered, and the solvent was removed on a rotatory evaporator leaving 90 g of the desired product as an amber oil which was used without further purification.

EXAMPLE 2

Photographic films containing various amounts of the compounds of this invention were prepared using a standard high speed negative gold- and sulfur-sensitized gelatino-silver iodobromide emulsion.

A large sample of the unmodified emulsion was divided into smaller samples containing 0.15 moles of silver halide. Just prior to being coated, the emulsion samples were melted on a steam bath and the compounds to be tested for development modification were added as solutions in either tetrahydrofuran or water. Samples to which no modification had been done were also coated as controls against which to compare the effect of the development modifiers. The control samples and the modified emulsion samples were individually coated on gel-subbed polyethylene terephthalate film base (coating wt.=100 mg/dm² of AgBr) and after brief warm air drying, a standard protective overcoat was applied which consisted of a thin layer of gelatin hardened with chrome alum and formaldehyde.

To ensure that proper hardening had occurred, the film samples were allowed to age at room temperature for several days, at which time the melting points of the emulsions were obtained. Samples of each film were carefully marked with a soft pencil and suspended in distilled water on a hot plate. The temperature of the water was slowly raised (ca. 1° F./minute) and the temperature at which the overcoat dissolved was noted by the disappearance of the pencil mark. The melting point of the emulsion layer was taken as the temperature at which it sloughed off of the film base.

Coating weights of all films were obtained by a standard titration technique on duplicate samples taken from areas of the films which were as close as possible to the areas which were to be subjected to the sensitometric examination described below. These coating weights were used to adjust to a common coating weight basis the pertinent sensitometric properties, such as Dmax, of the samples and controls.

The sensitometric properties of all of the films were obtained by (1) subjecting samples to a 2-second flash exposure, through a standard photographic step wedge, in a CRONEX sensitometer (exposure device available from Du Pont Photo Products, Wilmington, DE 19898), (2) processing in a standard hydroquinone-phenidone medical x-ray film developer under the conditions of time, temperature and equipment noted, and (3) completing the processing by standard fixing, rinsing and drying as noted. Control samples were processed under identical conditions. The density readings on the processed strips were recorded point-by-point using a densitometer. The data were corrected point-by-point for any difference in coating weight between the sample film and the control and were then plotted to yield a characteristic D-log E curve. Comparison of these curves with those of the control films allowed an assessment of the development modification imparted by compounds of this invention at a particular set of conditions, including level of addition, mode of addition and processing conditions. As will be seen from the data below, masked development/image modifiers imparted improved properties, such as increased silver utilization, to silver halide films without adversely affecting other sensitometric properties.

A 0.4% aqueous solution of the potassium salt of compound 7 was prepared. It was added to the emulsion in the amounts indicated in Table I. Exposed samples of the films were tray developed for 3 minutes at 20° C. and then fixed for 2 minutes.

TABLE I

| Add Level g/mol AgX | Dmax |
|---|---|
| none | 3.6 |
| 0.26 | 4.7 |
| 0.67 | 4.5 |
| 1.30 | 4.4 |

The other sensitometric properties were not adversely affected. As larger amounts are used the decrease in maximum density is believed to be caused by the restraining action of excess PMT. Similar results were obtained when samples were processed for 18 to 25 seconds at 33° C. in an X-OMAT automatic processer.

EXAMPLE 3

Compounds 3, 9, and 10, which are not water-soluble, were added to emulsion as tetrahydrofuran solutions. Films were prepared and tested as in Example 2 and comparative results are given in Table II.

TABLE II

| Compound Added | Add Level g/mol AgX | Dmax |
|---|---|---|
| none | — | 3.40 |
| 3 | 0.67 | 3.76 |
| 9 | 1.30 | 3.84 |
| 10 | 1.30 | 3.68 |

While these results show an improvement relative to the control, they are not as dramatic as those obtained with compound 7 in Example 2.

EXAMPLE 4

Compound 7 was added to the emulsion as a tetrahydrofuran solution of its free acid form in the same amounts as in Example 2. The resulting increase in top density was less than observed in Example 2 and at a level of 1.30 g/mol of silver halide the top density was actually lower than the control. These results suggest that water-soluble salts are superior for the practice of the present invention.

EXAMPLE 5

Samples of machine processed films were selected for detailed examination of the origin of the increase in observed Dmax resulting from the addition of compound 7. The actual amount of developed silver in a given area of the processed film was determined (g/m²) with a panalyzer. The covering power (CP) of the developed silver in the films was determined and is defined as, $$CP = \frac{Dmax}{Ag°}$$

where Dmax was the average of 15 readings on each of two separate samples of each film which had received a Dmax exposure before processing, and Ag° was the amount of silver in g/m² in these same films as determined by averaging 12 panalyzer readings on each of two samples. These data were also used to calculate the amount of silver halide originally present in the films that was actually utilized. This value, termed "silver utilization", is defined as, $$\text{Silver Utilization} = \frac{Ag°}{AgBr \times 0.574}$$

where Ag° is the same as previously described for covering power, AgBr is the weight of silver bromide in the unprocessed film in g/m² as determined by standard titration methods, and 0.574 is a factor which converts AgBr to its equivalent in silver only. Therefore, $$\text{Silver Utilization} = \frac{\text{Silver in processed film given a } Dmax \text{ exposure}}{\text{Silver in unprocessed film}}$$

Table III gives the improvement, relative to controls, in Dmax, covering power, and silver utilization which result from the addition of sodium and potassium salts of Compound 7 to the emulsion prior to coating. The addition level in both cases was 0.26 gm/mole of silver halide. The exposed films were processed at 33° C. for 19 seconds in an X-OMAT automatic processor.

TABLE III

| Addition | % Increase in Dmax | % Increase in CP | % Increase in Silver Utilization |
| --- | --- | --- | --- |
| K salt cpd 7 | 11% | 9% | 5% |
| Na salt cpd 7 | 18% | 11% | 5% |

It can be seen from Table III that the increase in image density imparted to these films by addition of compound 7 of this invention can be attributed (1) to an increase in the amount of silver utilized during the development, and (2) the increased efficiency of the silver in producing an image.

EXAMPLE 6

Aqueous solutions were prepared of the potassium salts of compounds 7 and 8, along with the sodium salt of compound 7. These were incorporated in emulsions and samples were prepared and tested as in Example 2. Table IV gives comparative results.

TABLE IV

| Addition | g/mole AgX | Covering (CP) | % Increase in CP |
| --- | --- | --- | --- |
| None | — | 0.53 | — |
| Na salt cpd 7 | 0.30 | 0.59 | 11% |
| K salt cpd 7 | 0.30 | 0.58 | 9% |
| K salt cpd 8 | 0.07 | 0.58 | 9% |
| None | — | 0.53 | — |

These results show that different water-soluble salts are effective and that compound 8 is a much more active electron acceptor than compound 7. This is illustrated by the much lower amount required for equivalent increase in covering power. Compound 8 is a water-soluble version of compound 3.

EXAMPLE 7

Compound 7 was held at a pH of 10.2 for 24 hours without undergoing a cleavage reaction. This demonstrates the advantage of the masked compounds of the present invention over prior art compounds which cleave when placed in an alkaline solution such as a developer.

A wide variation in effective processing temperatures and times may be used with the compounds of this invention. Prior art modifiers rely on simple hydrolysis during development, a mode of release which is sensitive to temperature and time and unrelated to development. Since the compounds of this invention are hydrolytically stable and the release of the development active component is triggered only by electron transfer from developer oxidation products, the release is directly coupled to the amount of development and only indirectly to the conditions which are bringing about that development. Therefore, once the optimum level of addition is determined for a given beneficial effect under some set of processing conditions, this beneficial effect will be relatively insensitive to changes, either intended or unintended, in these processing conditions.

EXAMPLE 8

Based on the indication in Table IV that the sodium salt of compound 7 gave improved covering power, a larger scale experiment was run in order to produce sufficient film for long term evaluation. Table V gives comparative results after 3 months normal aging, followed by development in an X-OMAT automatic processor. The experiment employed the sodium salt of compound 7 in the amount of 33 mg/mole of silver halide.

TABLE V

| Film | Speed | Gradient | Dmax | Dmin | Melting Point Emulsion | Point Over-Coat | Covering Power |
| --- | --- | --- | --- | --- | --- | --- | --- |
| Control | 120 | 2.62 | 3.24 | .20 | 72 | 65 | .640 |
| Exper. | 129 | 2.32 | 3.30 | .20 | 73 | 65 | .667 |

These results confirm the improvement in covering power and Dmax which result from incorporation of the masked development/image modifier compounds of the present invention. The emulsion and abrasion melting points show that since the hardness of the aged films is equivalent, the improvement in covering power and Dmax must be attributed to the present invention.

We claim:

1. A masked compound of the formula

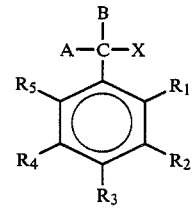

wherein A and B each represents hydrogen, alkyl, carboxyalkyl or alkyl carboxyalkyl, said alkyl moiety comprising 1-3 carbon atoms; each of $R_1$ to $R_5$ is a member selected from the group consisting of hydrogen, halogen, —$CF_3$, cyano, or nitro group, X is a radical with one of the following structures:

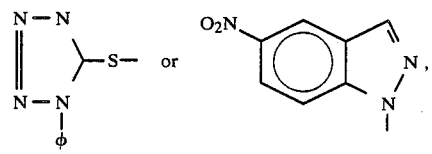

such that either 1-phenyl-5-mercaptotetrazole or 5-nitroindazole, is released by electron transfer: and wherein the $R_1$ to $R_5$-substituted ring has an electron withdrawing effect designated by a Hammet sigma function value of $\sigma = 0.50$ to $1.00$.

2. The compound of claim 1 in which $R_3 = NO_2$, and $R_1$, $R_2$, $R_4$, and $R_5$ are hydrogen.

3. The compound of claim 2 in which A is hydrogen and B = carboxyalkyl.

4. The compound of claim 1 wherein two of the $R_1$–$R_5$ groups are $NO_2$ groups, and the remainder are hydrogens.

5. The compound of claim 1 having the formula

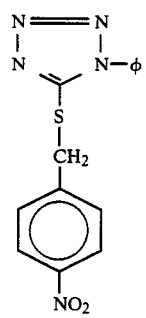

6. The compound of claim 1 having the formula

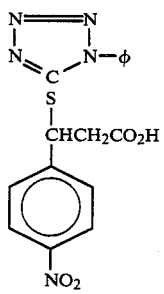

7. The compound of claim 1 having the formula

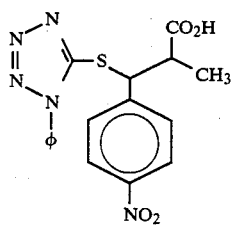

8. The compound of claim 1 having the formula

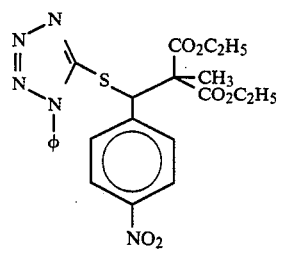

9. The compound of claim 1 having the formula

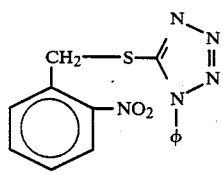

10. The compound of claim 1 having the formula

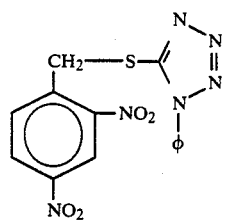

11. The compound of claim 1 having the formula

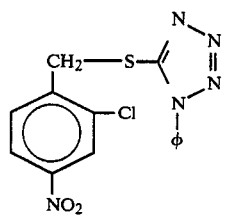

12. The compound of claim 1 having the formula

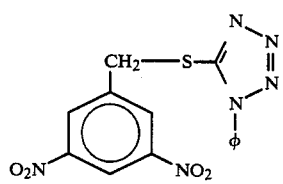

13. The compound of claim 1 having the formula

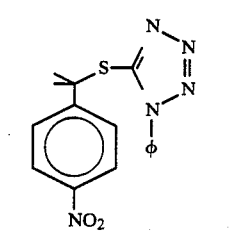

14. The compound of claim 1 having the formula

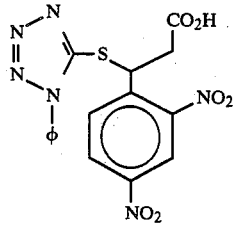

15. The compound of claim 1 having the formula

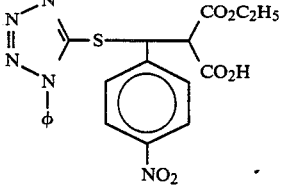

16. The compound of claim 1 having the formula
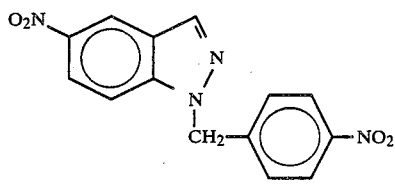
17. The compound of claim 1 having the formula
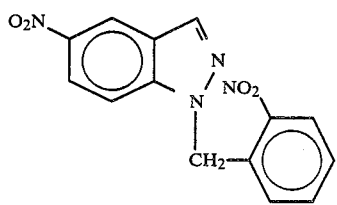
* * * * *

UNITED STATES PATENT OFFICE
CERTIFICATE OF CORRECTION

PATENT NO. : 4,501,896
DATED : February 26, 1985
INVENTOR(S) : Dennis Scott Donald and Ross Albert Lee It is certified that error appears in the above-identified patent and that said Letters Patent are hereby corrected as shown below:

| Column | Line | | |
|--------|------|---|---|
| 20 | 50 | left formula " 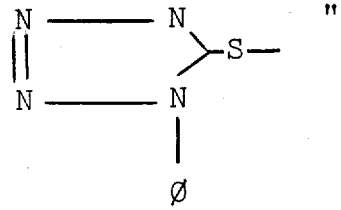 " |
| | | should be -- 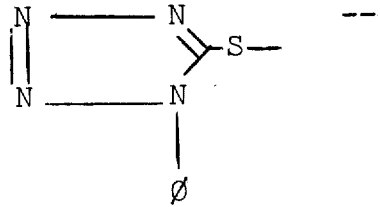 -- |

Signed and Sealed this

Twenty-fourth Day of September 1985

[SEAL]

Attest:

DONALD J. QUIGG

Attesting Officer

Commissioner of Patents and
Trademarks—Designate